United States Patent
Enger et al.

(10) Patent No.: US 11,638,566 B2
(45) Date of Patent: May 2, 2023

(54) NON-INVASIVE MEASUREMENT OF ARTERIAL INPUT FUNCTION FOR POSITRON EMISSION TOMOGRAPHY IMAGING

(71) Applicant: THE ROYAL INSTITUTION FOR THE ADVANCEMENT OF LEARNING/MCGILL UNIVERSITY, Montreal (CA)

(72) Inventors: Shirin Abbasi Nejad Enger, Montreal (CA); Gustavo Adolfo Vladimir Kertzscher Schwencke, Skurup (SE)

(73) Assignee: THE ROYAL INSTITUTION FOR THE ADVANCEMENT OF LEARNING/MCGILL UNIVERSITY, Montreal (CA)

( * ) Notice: Subject to any disclaimer, the term of this patent is extended or adjusted under 35 U.S.C. 154(b) by 682 days.

(21) Appl. No.: 16/611,388

(22) PCT Filed: May 31, 2018

(86) PCT No.: PCT/CA2018/050644
§ 371 (c)(1),
(2) Date: Nov. 6, 2019

(87) PCT Pub. No.: WO2018/218361
PCT Pub. Date: Dec. 6, 2018

(65) Prior Publication Data
US 2020/0163633 A1 May 28, 2020

Related U.S. Application Data

(60) Provisional application No. 62/513,157, filed on May 31, 2017.

(51) Int. Cl.
*A61B 6/00* (2006.01)
*A61B 6/03* (2006.01)
(Continued)

(52) U.S. Cl.
CPC .......... *A61B 6/4241* (2013.01); *A61B 6/037* (2013.01); *A61B 6/507* (2013.01); *G01T 1/1603* (2013.01);
(Continued)

(58) Field of Classification Search
CPC ....... A61B 6/4241; A61B 6/037; A61B 6/507; G01T 1/1603; G01T 1/164; G01T 1/172;
(Continued)

(56) References Cited

U.S. PATENT DOCUMENTS

| 4,413,184 A | 11/1983 | Marrone |
| 5,880,475 A | 3/1999 | Oka et al. |

(Continued)

FOREIGN PATENT DOCUMENTS

| JP | 09-80156 | 3/1997 |
| JP | 09-197050 | 7/1997 |

(Continued)

OTHER PUBLICATIONS

Extended European Search Report dated Dec. 17, 2020 in counterpart EP application.
(Continued)

*Primary Examiner* — David P Porta
*Assistant Examiner* — Gisselle M Gutierrez
(74) *Attorney, Agent, or Firm* — Norton Rose Fulbright Canada LLP

(57) ABSTRACT

Methods and systems for establishing a kinetic model input function (IF) in positron emission tomography and single-photon emission computed tomography are provided. A position of interaction along a scintillating fiber coil is determined by: detecting a first plurality and second plurality of photons at first and second ends of the scintillating fiber coil; associating the first plurality of photons and the second plurality of photons with the interaction event based
(Continued)

on a timing parameter; and determining a position of interaction for the interaction event based on a comparison between a first parameter of the first plurality of photons and a second parameter of the photons in the second plurality of photons.

19 Claims, 9 Drawing Sheets

(51) Int. Cl.
G01T 1/164 (2006.01)
G01T 1/29 (2006.01)
G01T 1/172 (2006.01)
G01T 1/20 (2006.01)
G21K 1/02 (2006.01)
G01T 1/16 (2006.01)

(52) U.S. Cl.
CPC .............. *G01T 1/164* (2013.01); *G01T 1/172* (2013.01); *G01T 1/201* (2013.01); *G01T 1/2985* (2013.01); *G21K 1/02* (2013.01)

(58) Field of Classification Search
CPC ......... G01T 1/201; G01T 1/2985; G21K 1/02; G01R 33/481
See application file for complete search history.

(56) References Cited

U.S. PATENT DOCUMENTS

| 6,510,336 | B1* | 1/2003 | Daghighian | A61B 6/4258 250/370.06 |
| 6,602,488 | B1* | 8/2003 | Daghighian | A61K 51/1282 424/9.1 |
| 9,268,045 | B2* | 2/2016 | Nakamura | G01T 3/06 |
| 2004/0116807 | A1* | 6/2004 | Amrami | A61B 6/425 600/436 |
| 2009/0218502 | A1* | 9/2009 | Axelsson | A61B 6/4258 250/370.11 |
| 2017/0222728 | A1* | 8/2017 | Baiden | H04B 10/11 |

FOREIGN PATENT DOCUMENTS

| JP | 2014020902 | 2/2014 |
| WO | 2017010896 | 1/2017 |
| WO | 2017072030 | 5/2017 |

OTHER PUBLICATIONS

Chie Seki et al., "Application of a beta microprobe for quantification of regional cerebral blood flow with 15O-water and PET in rhesus monkeys", Annals of Nuclear Medicine, 1998, vol. 12, No. 1, pp. 7-14.

International Search Report and Written Opinion dated Aug. 3, 2018 in connection with International application No. PCT/CA2018/050644.

Hinz, "Input functions in PET", A Pioneering Research Institue at The University of Manchester, Wolfson Molecular Imaging Centre, http://personalpages.manchester.ac.uk/staff/rainer.hinz/material/petif07.html.

Villanueva et al., "Spatial resolution of a noninvasive measurement of the arterial and venous input function using a wrist monitor", IEEE 2004, pp. 2232-2236.

Litton et al., "Transcutaneous measurement of the arterial input function in positron emission tomography", IEEE Transanctions on Nuclear Science, vol. 37, No. 2, Apr. 1990, pp. 627-628.

Watabe et al., "Development of skin surface radiation detector system to monitor radioactivity in arterial blood along with positron emission tomography", IEEE Transactions on Nuclear Science, vol. 42, No. 4, Aug. 1995, pp. 1455-1459.

Yamamoto et al., "Preliminary study for the development of a tweezers-type coincidence detector for tumor detection", Nuclear Instruments and Methods in Physics Research A 548, 2005, pp. 564-570.

Yamamoto et al., "Development of a tweezers-type coincidence imaging detector", Ann Nucl Med 22, 2008, pp. 387-393.

Yamamoto et al., "Imaging of an artery from skin surface using beta camera", IEEE Transactions on Nuclear Science, vol. 46, No. 3, Jun. 1999, pp. 583-586.

Su et al., "Noninvasive estimation of the arterial input function in positron emission tomography imaging of cerebral blood flow", Journal of Cerebral Blood Flow & Metabolism 33, 2013, pp. 115-121.

Pain et al., "Arterial Input Function Measurement Without Blood Sampling Using a ß-Microprobe in Rats", The Journal of Nuclear Medicine, vol. 45, No. 9, Sep. 2004, pp. 1577-1582.

Kriplani et al., "Non-invasive and selective measurement of the arterial input function using a PET Wrist Scanner", IEEE Nuclear Science Symposium Conference Record, M14-312, 2006, pp. 3266-3270.

Lee et al., "A positron-probe system for arterial input function quantification for positron emission tomography in humans", Review of Scientific Instruments, 79, 064301, 2008, pp. 1-7.

Nakamura et al., "Development of position-sensitive scintillation neutron detectors at J-PARC-MLF", JAEA-Conf 2015-002, pp. 391-398.

Office Action dated Jan. 8, 2021 in counterpart JP application.

\* cited by examiner

NON-INVASIVE MEASUREMENT OF ARTERIAL INPUT FUNCTION FOR POSITRON EMISSION TOMOGRAPHY IMAGING

CROSS-REFERENCE TO RELATED APPLICATIONS

The present application claims the benefit of U.S. Provisional Patent Application No. 62/531,157 filed on May 31, 2017, the contents of which are hereby incorporated by reference.

TECHNICAL FIELD

The present disclosure relates generally to imaging techniques, and more particularly to the acquisition of an input function (IF) for use with positron emission tomography (PET) imaging, single-photon emission computed tomography (SPECT), and PET-magnetic resonance imaging (PET-MRI).

BACKGROUND OF THE ART

PET, SPECT and PET-MRI are functional imaging techniques using radioactive tracers to obtain anatomical and physiological information in a target volume. The PET technique is based on detection of positron-electron annihilation events and the SPECT technique is based on detection of gamma emission events. When performing a PET scan, a positron (β+) emitting radioactive tracer (also known as a radiotracer) is administered to the patient before or during the scan and the interaction of that molecule with the body's physiological processes can be monitored. A SPECT scan monitors physiological processes similarly to the PET scan, however, the SPECT scan uses a radiotracer that emits photons via gamma events. PET-MRI is a hybrid imaging technology that incorporates magnetic resonance imaging (MRI), soft tissue morphological imaging and PET functional imaging.

Images acquired with PET, SPECT, and PET-MRI are composite of various superimposed signals where only one is of interest. The desired signal may describe a tracer bound to a particular receptor or the amount of tracer trapped at the site of metabolism. In order to isolate the desired component of the signal, mathematical kinetic models are used. These models relate the dynamics of the tracer molecule and all its possible states (compartments) to the resultant PET/SPECT/PET-MRI image.

Mathematical kinetic models require an IF. The concentration of the unchanged (non-metabolized) compound in arterial plasma as a function of time is one such IF and is often referred to as a plasma time-activity curve (PTAC). The traditional manner to obtain the IF is invasive, i.e. arterial blood can be withdrawn by manual or automated blood sampling. There are many issues that accompany this technique, including discomfort to the patient, increased risk of transferring a blood-borne disease, and the need for additional personnel and equipment in withdrawing and assaying the plasma samples.

Therefore, there is a need for a non-invasive technique to acquire the IF. While some non-invasive techniques have been proposed, they have issues with background rejection and spatial resolution. Improvement is desired.

SUMMARY

In accordance with a broad aspect, there is provided a method for determining a position of interaction along a scintillating fiber coil, comprising: detecting a first plurality and second plurality of photons at first and second ends of the scintillating fiber coil, respectively, the first and second pluralities of photons produced by an interaction event between a radiotracer and the scintillating fiber coil; associating the first plurality of photons and the second plurality of photons with the interaction event based on a timing parameter; and determining a position of interaction for the interaction event based on a comparison between a first parameter of the first plurality of photons and a second parameter of the second plurality of photons.

In accordance with another broad aspect, there is provided a method for establishing a kinetic model input function in one of positron emission tomography and single-photon emission computed tomography, comprising: performing the method of determining a position of interaction along a scintillating fiber coil above multiple times for a plurality of interaction events to obtain a plurality of positions of interaction; and establishing the kinetic model input function based on the plurality of positions of interaction.

In some embodiments, the method further comprises measuring a level of background radiation proximate the scintillating fiber coil, wherein determining a position of interaction comprises adjusting the first and second levels of attenuation based on the level of background radiation.

In some embodiments, detecting the first plurality and second plurality of photons produced by the scintillating fiber coil comprises receiving the first and second pluralities of photons via an optical fiber.

In some embodiments, an attenuation coefficient of the optical fiber is lower than an attenuation coefficient of the scintillating fiber coil.

In some embodiments, detecting the first plurality and second plurality of photons produced by the scintillating fiber coil comprises determining, via a coincidence detector, that the first plurality of photons and the second plurality of photons are produced by the interaction event based on a time of receipt of the first plurality of photons and of the second plurality of photons.

In some embodiments, the first and second parameters are first and second attenuation levels, respectively.

In some embodiments, the method further comprises positioning the scintillating fiber coil to substantially cover a portion of a body.

In some embodiments, the portion of the body is a wrist.

In some embodiments, the method further comprises administering the radiotracer.

In accordance with a further broad aspect, there is provided a device for establishing a kinetic model IF in positron emission tomography and single-photon emission computed tomography, comprising: a scintillating fiber coil arranged for substantially covering a portion of a body, the scintillating fiber coil having a first end and a second end; at least one photon detector optically connected to the first and second ends of the scintillating fiber coil; and a processing device communicatively coupled to the at least one photon detector and configured for: for each of a plurality of interaction events between the scintillating fiber coil and a radiotracer: detecting first and second pluralities of photons at first and second ends of the scintillating fiber coil, respectively, the first and second pluralities of photons produced by the interaction event; associating the first plurality of photons and the second plurality of photons with the interaction event based on a timing parameter; and determining a position of interaction for the interaction event based on a comparison between a first parameter of the first plurality of photons and a second parameter of the second plurality of photons; and establishing a kinetic model input function based on the positions of interaction.

In some embodiments, the device further comprises an ambient radiation monitor communicatively coupled to the processing device, wherein the processing device is further configured for obtaining a measurement of a level of background radiation proximate the scintillating fiber coil from the ambient radiation monitor, and wherein determining a position of interaction comprises adjusting the first and second levels of attenuation based on the level of background radiation.

In some embodiments, the level of background radiation comprises radiation produced by the body.

In some embodiments, the device further comprises an optical fiber, wherein the at least one photon detector is optically connected to the first and second ends of the scintillating fiber coil via the optical fiber.

In some embodiments, an attenuation coefficient of the optical fiber is lower than an attenuation coefficient of the scintillating fiber coil.

In some embodiments, the device further comprises a coincidence detector, wherein the processing device is configured for operating the coincidence detector to detect the first plurality and second plurality of photons produced by the scintillating fiber coil to determine that first plurality of photons and the second plurality of photons are produced by the interaction event based on a time of receipt of the first plurality of photons and of the second plurality of photons.

In some embodiments, the first and second parameters are first and second attenuation levels, respectively.

In some embodiments, the portion of the body is a wrist.

In some embodiments, the device further comprises a subsequent scintillating fiber coil optically connected to the at least one photon detector, wherein the processing device is further configured for performing the steps of detecting, associating, and determining for third and fourth pluralities of photons for a subsequent plurality of interaction events between the subsequent scintillating fiber coil and the radiotracer.

In some embodiments, wherein the subsequent scintillating fiber coil is arranged for substantially covering a subsequent portion of the body at least in part different from the portion of the body.

BRIEF DESCRIPTION OF THE DRAWINGS

Further features and advantages of the present invention will become apparent from the following detailed description, taken in combination with the appended drawings, in which.

It will be noted that throughout the appended drawings, like features are identified by like reference numerals.

DETAILED DESCRIPTION

Figure 1:
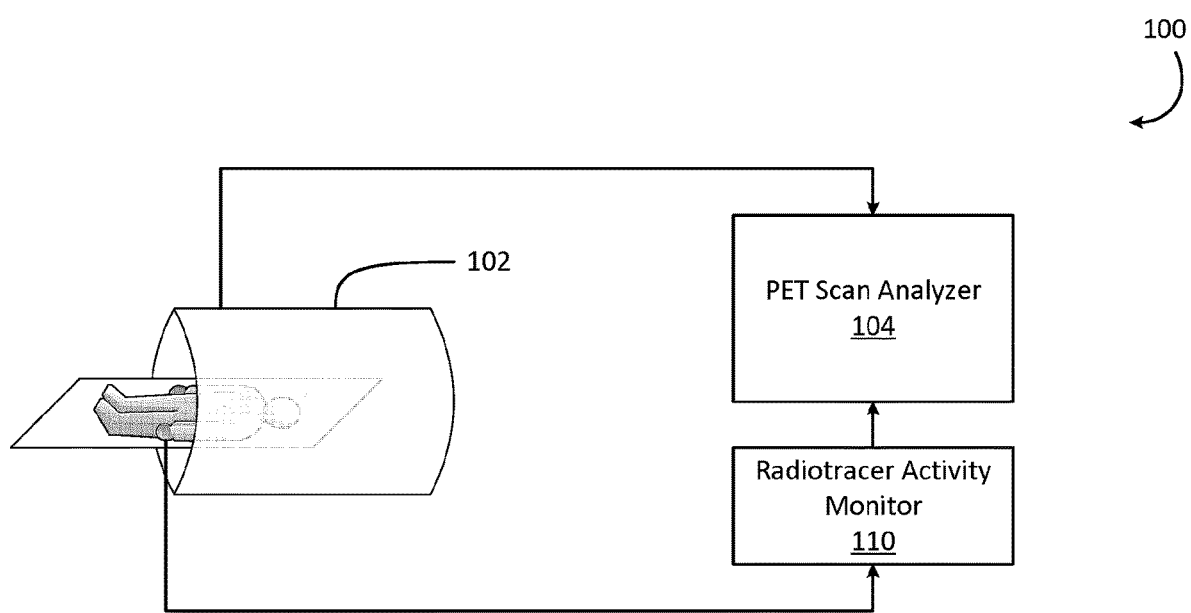
FIG. 1 is a diagram illustrating an example PET scan system or a SPECT scan system or PET-MRI scan system.

With reference to FIG. 1, a scan system 100 is shown. The scan system 100 may be a PET scan system, a SPECT scan system, or a PET-MRI scan system. The scan system 100 includes a scanner 102, a scan analyzer 104, and a radiotracer activity monitor 110. The scanner 102 can be any suitable PET/SPECT/PET-MRI scanner providing PET/SPECT/PET-MRI scan data to the scan analyzer 104, and the scan analyzer 104 can be any suitable computer or processing system configured for analyzing the PET/SPECT/PET-MRI scan data received from the scanner 102, including by implementing mathematical kinetic models used to isolate desired components of the signals received from the scanner 102. The mathematical kinetic models implemented by the scan analyzer 104 require an input function (IF). The IF is supplied to the scan analyzer 104 by the radiotracer activity monitor 110.

Figure 2:
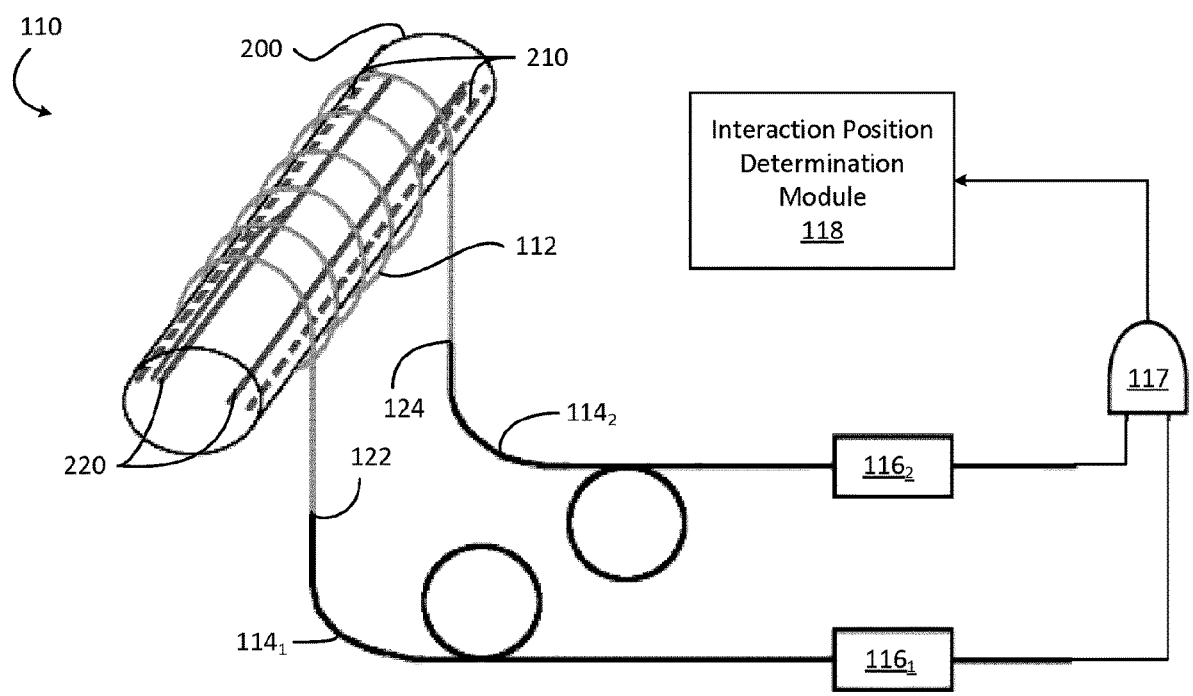
FIG. 2 is a block diagram illustrating a first embodiment of a radiotracer activity monitor.

With reference to FIG. 2, an embodiment of the radiotracer activity monitor 110 is shown. The radiotracer activity monitor 110 includes a scintillating fiber coil 112 having first and second ends, a pair of fiber optic cables 114₁, 114₂ connected at each end of the scintillating fiber coil 112, a pair of photon detectors 116₁, 116₂, each connected to a respective one of the fiber optic cables 114₁, 114₂, a coincidence detector 117 connected to the photon detectors 116₁, 116₂, and an interaction position determination module 118, to which the coincidence detector 117 is connected.

The scintillating fiber coil 112 is an optical fiber or other light-guiding filament having first and second ends 122, 124 and which is shaped into a plurality of spaced curved patterns, for example circular-shaped loops, S-shaped patterns, zigzag patterns, and the like. The spacing between the curved patterns may be constant or vary along the length of the scintillating fiber coil 112, and the scintillating fiber coil 112 has any suitable number of curved patterns and of any suitable size. In some embodiments, the bending radius of the scintillating fiber coil is constant to generate a constant light attenuation constant within the scintillating fiber coil. In some embodiments, the configuration of the scintillating fiber coil 112 is substantially fixed, and in other embodiments one or more of the spacing, size, and/or count of the curved patterns is adjustable. In some embodiments, the scintillating fiber coil 112 is mounted around or retained within a rigid structure. For example, a cylindrical shell featuring a spiral or cylindrical bore for receiving the scintillating fiber coil can be provided. The shell can be sized for receiving a body part, and can optionally include an inflatable bladder or similar device for securing the body part within the shell. In some cases, the shell can be produced by 3D printing.

The curved patterns of the scintillating fiber coil 112 are configured for receiving or otherwise having inserted therein a portion 200 of a body, for example of a human patient, an animal patient, or any other suitable patient. In some embodiments, the scintillating fiber coil 112 substantially encircles the portion 200. In other embodiments, the scintillating fiber coil 112 substantially covers part or all of the portion 200. The portion 200 may be a wrist, an arm, an ankle, a leg, a neck, a torso, or any other suitable portion.

Running within the portion 200 of the body are at least one artery 210, illustrated by the dashed lines, and/or at least one vein 220, illustrated by the unbroken lines. In some embodiments, the scintillating fiber coil 112 is positioned to be proximate or in contact with a surface of the portion 200 of the body, for example proximate or in contact with a skin surface of the portion 200. In some embodiments, a collimator is placed between the scintillating fiber coil 112 and the skin surface of the portion 200. In some embodiments, the curved patterns of the scintillating fiber coil 112 are positioned to increase the number of loops around sections of the portion 200 where the one or more arteries 210 and/or veins 220 are closest to the surface of the portion 200. In other embodiments, the curved patterns of the scintillating fiber coil 112 are distributed substantially evenly along the portion 200.

Figure 3A:
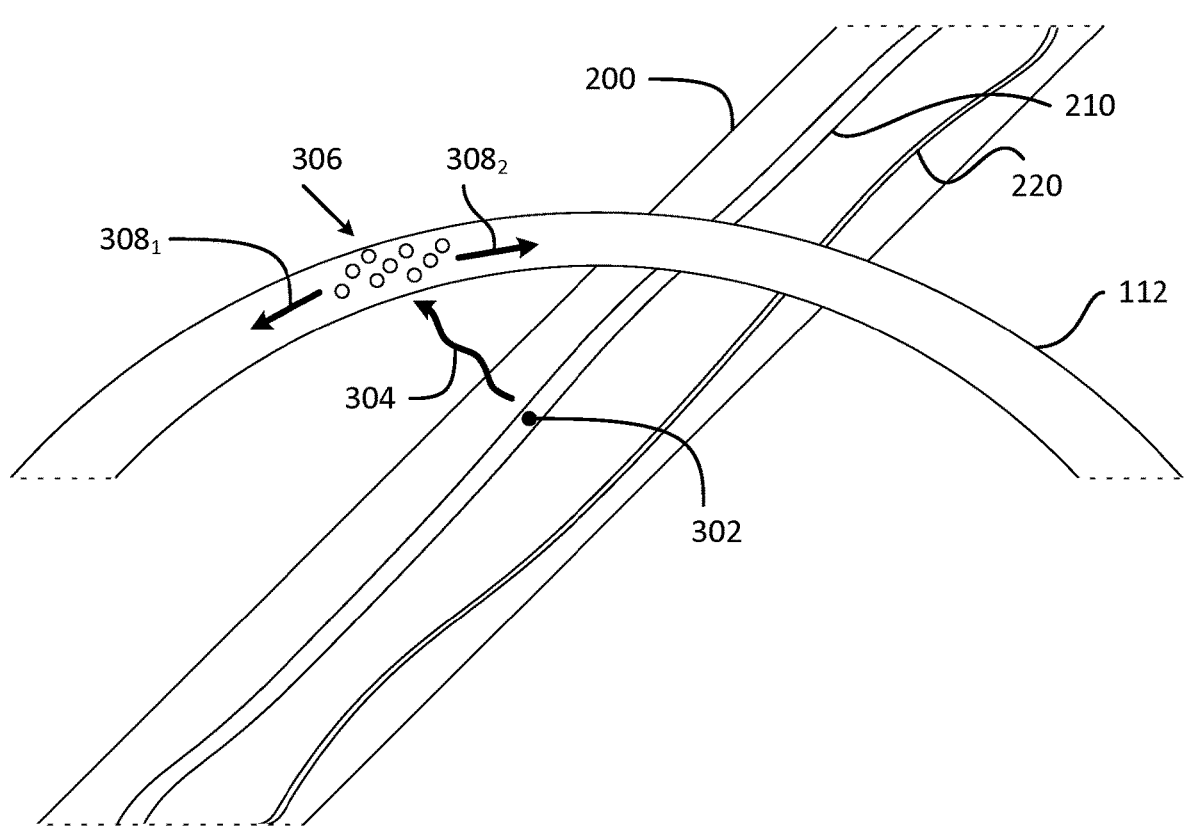
FIG. 3A is a block diagram illustrating an example positron-electron disintegration emission.
Figure 3B:
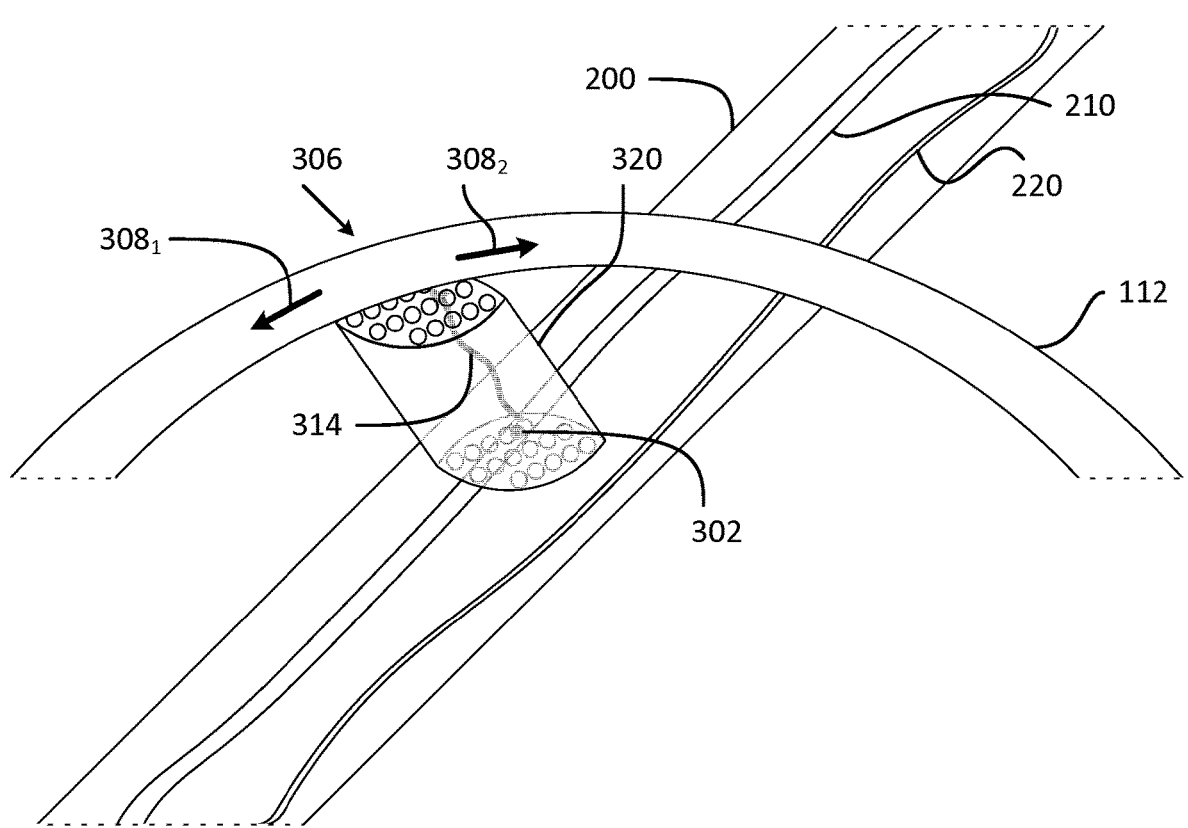
FIG. 3B is a block diagram illustrating an example photon emission.

With reference to FIGS. 3A and 3B, the scintillating fiber coil 112 incorporates a radioluminescent material, that is to say a material comprising a plurality of molecules 306 which emit light when the molecules 306 absorb radiation. This can include alpha radiation, beta radiation, gamma radiation, any suitable combination thereof, or any other suitable kind of radiation. The scintillating fiber coil 112 may be made of any one or more of glass, plastic, crystal, or in some cases may be a tube or other container filled with a liquid material. The radioluminescent material may be embedded within the scintillating fiber coil 112, for example the scintillating fiber coil 112 includes an organic material, for example BCF-12™ and/or BCF-60™. Alternatively, the radioluminescent material can be obtained in powder form, mixed with an adhesive, and then applied to a surface of the scintillating fiber coil 112. Examples of radioluminescent materials in powder form include inorganic scintillators $Y_2O_3$:Eu and $Gd_2O_2S$:Tb. In some embodiments, a range of diameter of the scintillating fiber coil 112 is less than or equal to 5 mm. In other embodiments, other diameters of the scintillating fiber coil 112 are considered. The scintillating fiber coil 112 may have any suitable cross-section. When a positron or other radioactive particle collides with, or otherwise interacts with, the scintillating fiber coil 112, the molecules 306 of the scintillating fiber coil 112 produce a plurality of photons.

When a radiotracer is administered to the portion 200 of the body, or to the body generally, radiotracer particles, for example the particle 302, will flow through the artery 210. In some embodiments, the radiotracer can be any suitable positron-emitting radiotracer for administering to a body, including isotopes of carbon, nitrogen, oxygen, fluorine, gallium, zirconium, rubidium, and the like. In other embodiments, the radiotracer can be any suitable photon emitting radiotracer for administering to a body, including isotopes of technetium, indium, iodine, and the like. Although the particle 302 is shown as flowing through the artery 210, it should be understood that the particle 320 can also flow through the vein 220. In addition, although the following discussion focuses on positron-emitting radiotracers, other types of radiotracers are considered.

With continued reference to FIG. 3A, in some embodiments the radiotracer particle 302 is a positron-emitting particle. When the radiotracer particle 302, flowing through the artery 210, emits a positron 304, the positron 304 may be directed toward the scintillating fiber coil 112. During traversal of the scintillating fiber coil 112, the positron 304 causes the molecules 306 to produce photons, which are emitted isotropically. A first plurality of the photons, illustrated by the arrow $308_1$, travels along the scintillating fiber coil 112 in a first direction, and a second plurality of the photons, illustrated by the arrow $308_2$, travels along the scintillating fiber coil 112 in a second direction opposite the first direction. Although the photons produced by the molecules 306 may scatter in multiple directions, the light-guiding properties of the scintillating fiber coil 112 cause at least some of the photons produced by the molecules 306 to form the first and second pluralities of photons $308_1$, $308_2$ which travel along the scintillating fiber coil 112 in opposite directions, as illustrated by the arrows.

In some embodiments, the distance between the superficial artery 210 or the vein 220 and the surface of the portion 200 is approximately 2-3 mm. Depending on the radiotracer used, positrons 304 emitted by the radiotracer particles 302 used for PET imaging have a range of travel distances in tissue which composes the portion 200. For example, positrons emitted from Fluorine-18 have a range of 2.6 mm, and positrons emitted from Gallium-68 have a range of 10.3 mm. In embodiments which use a positron-emitting radiotracer, the scintillating fiber coil 112 is placed in close proximity to the surface of the portion 200. This may facilitate collisions between the emitted positrons 304 and the radioluminescent molecules 306 in the scintillating fiber coil 112.

With continued reference to FIG. 3B, in some other embodiments the radiotracer particle 302 is a photon-emitting particle. In this embodiment, the radiotracer activity monitor 110 includes a microcollimator 320 which is located between the surface of the portion 200 and the scintillating fiber coil 112. The microcollimator 320 is made of a high-density material which is placed in contact with a surface of the portion 200 and which connects to the scintillating fiber coil 112. The microcollimator 320 is provided with a plurality of lengthwise holes which traverse the microcollimator 320, which serve to narrow and/or focus photons from the portion 200 which is incident the microcollimator 320. When the radiotracer particle 302, flowing through the artery 210, emits a photon 314, the photon 314 is directed within the microcollimator 320 and carried to the scintillating fiber coil 112. It should be noted that the photons emitted by the radiotracer, including the photon 314 emitted by the radiotracer particle 302, are emitted isotropically, that is to say substantially uniformly in all directions. The microcollimator 320 is configured to direct a subset of the emitted photons via the holes in the microcollimator 320 to the scintillating fiber coil 112. The subset of photons is then collected by the scintillating fiber coil 112 and transmitted as the pluralities of photons $308_1$, $308_2$ along the scintillating fiber coil 112.

With continued reference to FIG. 2, the pluralities of photons $308_1$, $308_2$ travel along the scintillating fiber coil 112 toward the ends 122, 124 of the scintillating fiber coil 112. Connected at the first end 122 of the scintillating fiber coil 112 is the photon detector $116_1$, and connected at the second end 124 of the scintillating fiber coil 112 is the photon detector $116_2$. The photon detectors $116_1$, $116_2$ may be implemented as photomultiplier tubes, silicon photomultipliers, avalanche photodiodes, PIN diodes, and the like, or any other suitable type of photodetector. In some embodiments, one photon detector can be used to implement both the photon detector $116_1$ and the photon detector $116_2$. In embodiments where two separate photon detectors $116_1$, $116_2$ are used, the first plurality of photons $308_1$ is detected by the photon detector $116_1$, and the second plurality of photons $308_2$ is detected by the photon detector $116_2$. In embodiments where one photon detector is used, the one photon detector is connected to both ends 122 and 124 of the scintillating fiber coil 112 and detects both the first and the second pluralities of photons $308_1$, $308_2$. In some embodiments, at least some of the scintillating fiber coil 112, the fiber optic cables $114_1$ and $144_2$, and the photon detectors $116_1$ and $116_2$ are retained within a structure that substantially prevents stray photons from light sources, for example nearby lamps or the sun, from interfering with the photons $308_1$, $308_2$ travelling along the scintillating fiber coil 112.

In some embodiments, the first end 122 of the scintillating fiber coil 112 is connected to the fiber optic cable $114_1$, and the second end 124 of the scintillating fiber coil 112 is connected to the fiber optic cable $114_2$. The fiber optic cables $114_1$, $114_2$ carry the pluralities of photons $308_1$, $308_2$ toward the photon detectors $116_1$, $116_2$. The fiber optic cables $114_1$ and $114_2$ are used to carry the pluralities of photons $308_1$, $308_2$ to the photon detectors $116_1$ and $116_2$ when the photon detectors $116_1$ and $116_2$ are located remotely from the portion 200. Distancing the photon detectors $116_1$ and $116_2$ from the portion 200 may help to avoid contaminating signal interference by other emitted particles, for example by the radiotracer. In addition, in embodiments where the scanner 102 is a PET-MRI scanner, there are restrictions on the presence of magnetic materials in proximity to the scanner 102. The fiber optic cables $114_1$, $114_2$ are used to convey the pluralities of photons $308_1$, $308_2$ away from the scanner 102, for example to an adjacent or remote room where the photon detectors $116_1$, $116_2$ and/or other components of the scan system 100. In other embodiments, the first and second ends 122, 124 of the scintillating fiber coil 112 are connected to the photon detectors $116_1$, $116_2$ without the fiber optic cables $114_1$, $114_2$. In some such embodiments, the photon detectors $116_1$ and $116_2$ can be provided with shielding to avoid contamination by the other emitted particles.

Due to the material properties of the material which constitutes the scintillating fiber coil 112, the photons of the pluralities of photons $308_1$, $308_2$ are subjected to an attenuation effect, which is manifested by the absorption of at least some of the photons of the pluralities of photons $308_1$, $308_2$ as the pluralities of photons $308_1$, $308_2$ travel along the scintillating fiber coil 112. The rate at which the scintillating fiber coil 112 absorbs photons of the pluralities of photons $308_1$, $308_2$ is defined as an attenuation coefficient, and is typically expressed as a decibel (dB) reduction in signal intensity. The fiber optic cables $114_1$, $114_2$ also subject the pluralities of photons $308_1$, $308_2$ to attenuation. In some embodiments, the attenuation coefficient of the scintillating fiber coil 112 is higher than the attenuation coefficient of the fiber optic cables $114_1$, $114_2$. For example, the attenuation coefficient of the scintillating fiber coil 112 is one, two, three, or more orders of magnitude higher than the attenuation coefficient of the fiber optic cables $114_1$, $114_2$. In some other embodiments, the attenuation coefficient of the scintillating fiber coil 112 is less than that of the fiber optic cables $114_1$, $114_2$. It should be noted that the scintillating fiber coil 112 and the fiber optic cables $114_1$, $114_2$ can have any suitable attenuation coefficient. In some embodiments, the attenuation coefficient for the scintillating fiber coil 112 and/or the fiber optic cables $114_1$, $114_2$ is selected to optimize the transmission of the pluralities of photons $308_1$, $308_2$. In other embodiments, the attenuation coefficient for the scintillating fiber coil 112 and/or the fiber optic cables $114_1$, $114_2$ is selected to limit an intensity of the pluralities of photons $308_1$, $308_2$.

The photon detectors $116_1$, $116_2$ each receive a respective one of the pluralities of photons $308_1$, $308_2$ as attenuated first by the scintillating fiber coil 112, and second by the respective fiber optic cables $114_1$, $114_2$. The photon detectors $116_1$, $116_2$ then transform the respective one of the pluralities of photons $308_1$, $308_2$ received into respective electrical signals. The photon detector $116_1$ transforms the first plurality of photons $308_1$ into a first electrical signal, and the photon detector $116_2$ transforms the second plurality of photons $308_2$ into a second electrical signal. The photon detectors $116_1$, $116_2$ can be any suitable type of photon detector, as described hereinabove.

The photon detectors $116_1$, $116_2$ are connected to the coincidence detector 117 which is configured for associating photons received at the photon detector $116_1$ with photons received at the photon detector $116_2$. More specifically, and with continued reference with FIG. 3A, when the positron 304 interacts with the scintillating fiber coil 112, the two pluralities of photons $308_1$ and $308_2$ are generated due to a common interaction event and sent along toward the photon detectors $116_1$, $116_2$. Similar behaviour occurs in the example of FIG. 3B. The coincidence detector 117 detects when the two pluralities of photons $308_1$ and $308_2$ are received at the photon detectors $116_1$, $116_2$ and associates the two pluralities of photons $308_1$ and $308_2$ to one another.

In some embodiments, the coincidence detector 117 operates on the electrical signals produced by the photon detectors $116_1$, $116_2$. For example, the coincidence detector 117 is configured to determine an electrical signal produced by the photon detector $116_1$ is received at the same time as an electrical signal produced by the photon detector $116_2$. In other embodiments, for example where the photon detectors $116_1$ and $116_2$ are implemented by a single photon detector, the functionality of the coincidence detector 117 is also provided by the single photon detector, and can operate on the received pluralities of photons $308_1$ and $308_2$ and/or on the electrical signals produced thereby.

The electrical signals produced by the photon detectors $116_1$, $116_2$ are sent to the interaction position determination module 118. In addition, information associating pluralities of photons $308_1$ and $308_2$ to one another produced by the coincidence detector 117 is sent to the interaction position determination module 118. The electrical signal and the information from the coincidence detector 117 can be sent via one or more wires, via one or more wireless communication pathways, or via any other suitable communication medium. The photon detectors $116_1$, $116_2$ and the coincidence detector 117 are equipped with any suitable communication interfaces for providing the electrical signals to the interaction position determination module 118.

The interaction position determination module 118 is configured for receiving the electrical signals produced by the photon detectors $116_1$, $116_2$ and the information produced by the coincidence detector 117, and for determining a position along the scintillating fiber coil 112 at which the positron 304 interacted with the one of the molecules 306 of the scintillating fiber coil 112, called a position of interaction, based on the electrical signals produced by the photon detectors $116_1$, $116_2$ and the associations between the pluralities of photons $308_1$ and $308_2$.

In some embodiments, the electrical signals provided to the interaction position determination module 118 are analog signals having respective amplitudes which are indicative of a photon count received by the photon detectors $116_1$, $116_2$. Put differently, the first electrical signal output by the photon detector $116_1$ has a first amplitude which is indicative of a number of photons present in the first plurality of photons $308_1$, and the second electrical signal output by the photon detector $116_2$ has a second amplitude which is indicative of a number of photons present in the second plurality of photons $308_2$. In some embodiments, the interaction position determination module 118 is configured to process the electrical signals received from the photon detectors $116_1$, $116_2$. For example, the interaction position determination module 118 amplifies the electrical signals output by the photon detectors $116_1$, $116_2$, for example using one or more op-amps. In another example, the interaction position determination module 118 performs an analog-to-digital conversion of the electrical signals output by the photon detectors $116_1$, $116_2$.

Once the electrical signals received from the photon detectors $116_1$, $116_2$ by the interaction position determination module 118 are processed, the interaction position determination module 118 associates the electrical signals with one another based on the information provided by the coincidence detector 117. The interaction position determination module 118 then compares parameters of the pluralities of photons $308_1$, $308_2$ to determine the position of interaction for the first and second pluralities of photons $308_1$, $308_2$.

In some embodiments, the interaction position determination module 118 determines the position of interaction based on relative degrees of attenuation of the first and second pluralities of photons $308_1$, $308_2$. If the plurality of photons $308_1$ is less attenuated than the plurality of photons $308_2$, then the position of interaction is closer to the end 122 than to the end 124 of the scintillating fiber coil, and vice-versa. For example, the interaction position determination module 118 uses an algorithm to determine the position of interaction. In some embodiments, the interaction position determination module 118 uses the function R(z)

$$R(z)=2z/\lambda_a=\ln(S_2/S_1)$$

to determine the position of interaction, where z is the position of interaction, $\lambda_a$ is the attenuation length of the scintillating fiber coil 112, $S_1$ is the amplitude of the electrical signal generated by the photon detector $116_1$, and $S_2$ is the amplitude of the electrical signal generated by the photon detector $116_2$.

In other embodiments, the interaction position determination module 118 determines the position of interaction based on a comparison of wavelength spectra of the first and second pluralities of photons $308_1$, $308_2$. For example, the interaction position determination module 118 compares the wavelength spectra for the plurality of photons $308_1$ in a given wavelength region to the wavelength spectra for the plurality of photons $308_2$.

The radiotracer activity monitor 110 determines the position of interactions between particles emitted by the individual radiotracer particles 302 and the scintillating fiber coil 112. Additionally, the radiotracer activity monitor 110 is configured for performing determinations regarding positions of interactions for multiple particle-scintillating fiber coil interactions, and is further configured for using the multiple positions of interactions to determine an IF for the mathematical kinetic models implemented by the PET/SPECT/PET-MRI scan analyzer 104. For example, the positions of interaction are used to determine the extent to which the radiotracer has traveled along the portion 200, a rate at which the radiotracer has traveled along or through the portion 200, or to determine a rate of emission of positrons by the radiotracer to establish a benchmark or standard of particle emission output by the radiotracer.

In some embodiments, the radiotracer activity monitor 110 uses the interactions within an initial time period of the radiotracer administration to determine a geometrical extent of the arteries 210 and veins 220 in the portion 200, as described in greater detail hereinbelow. The initial time period may last for any suitable duration, for example short enough to rule out radiotracer migration outside the arteries 210 and veins 220. In some embodiments, the measured geometrical extent of the arteries 210 and veins 220 is used throughout the remainder of a monitoring period during the PET/SPECT/PET-MRI scan, to rule out artificial ambient radiation, corresponding to radiotracer activity that originates from radiotracer particles outside the arteries 210 and veins 220.

Figure 4:
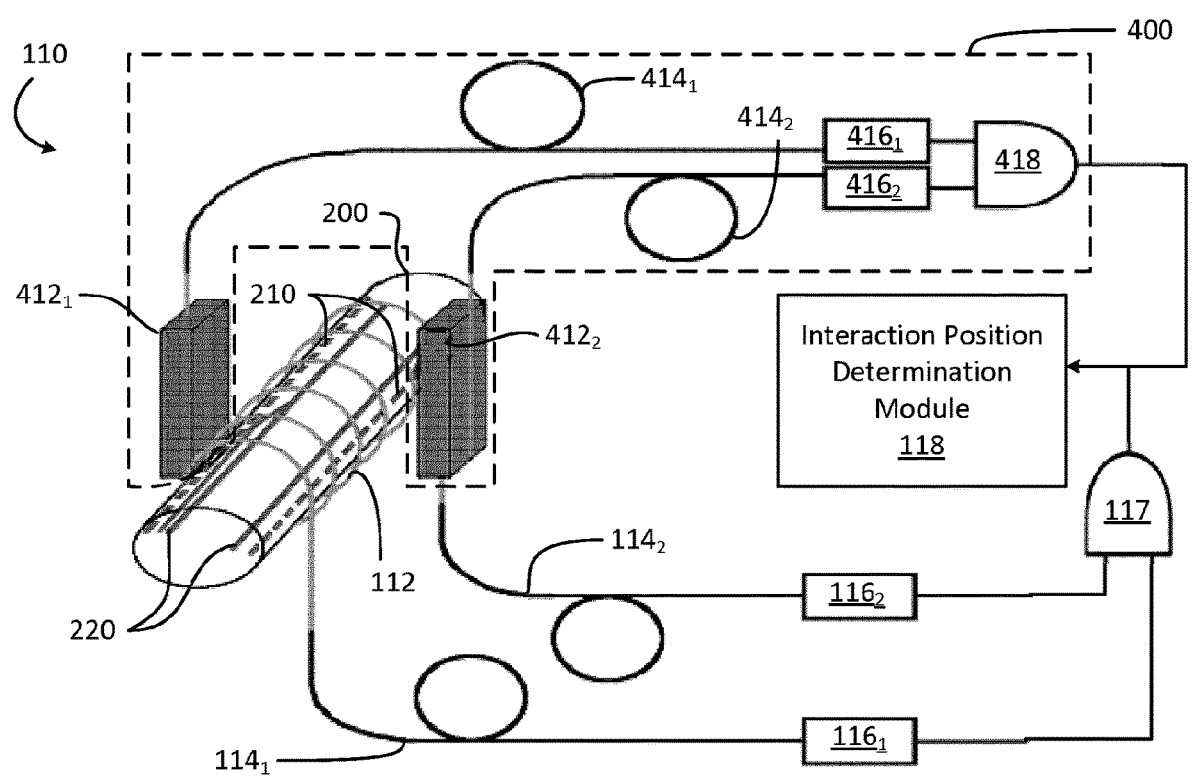
FIG. 4 is a block diagram illustrating a second embodiment of a radiotracer activity monitor.

With reference to FIG. 4, in some embodiments the radiotracer activity monitor 110 further includes an ambient radiation monitor 400. The ambient radiation monitor 400 includes a pair of radiation detectors $412_1$, $412_2$, a pair of transmission cables $414_1$, $414_2$, a pair of readout modules $416_1$, $416_2$, and a coincidence detector 418. The radiation detectors $412_1$, $412_2$ are each connected to a respective one of the readout modules $416_1$, $416_2$ by way of one of the transmission cables $414_1$, $414_2$. The radiation detectors $412_1$, $412_2$ are configured to produce signals which are carried by the transmission cables $414_1$, $414_2$ to the readout modules $416_1$, $416_2$ and to the coincidence detector 418. In some embodiments, the transmission cables $414_1$, $414_2$ are omitted and the radiation detectors $412_1$, $412_2$ are connected to the readout modules $416_1$, $416_2$ and to the coincidence detector 418.

In some embodiments, the ambient radiation monitor 400 is configured for determining a level of background radiation in the vicinity of the portion 200. In some other embodiments, the ambient radiation monitor 400 is configured for determining a level of artificial ambient radiation produced by the presence of the radiotracer in other portions of the body beyond the portion 200 and/or the presence of the radiotracer in the portion 200 other than in the artery 210 and/or the vein 220. In some embodiments, the ambient radiation monitor 400 is configured for determining both the level of background radiation and the level of artificial ambient radiation. The interaction position determination module 118 is provided with the level of background radiation and/or the level of artificial ambient radiation, which is used to further refine the determination of the positions of interaction. In some embodiments, the interaction position determination module 118 is configured to further refine the determination of the arterial IF based on the level of background radiation and/or the level of artificial ambient radiation.

In some embodiments, the radiation detectors $412_1$ and $412_2$ are connected to the readout modules $416_1$ and $416_2$ via respective transmission cables $414_1$, $414_2$. The radiation detectors $412_1$ and $412_2$ can be an ion chamber, scintillation detector, semiconductor detector, or any other suitable device for detecting radiation. The transmission cables $414_1$ and $414_2$ can be any suitable medium for transmitting information from the radiation detectors $412_1$ and $412_2$ to the photon detectors $416_1$ and $416_2$, including electric wire to transmit electric signals, fiber optic cables to transmit pluralities of photons, or any other suitable transmission medium. The readout modules $416_1$ and $416_2$ can be op-amps, photon detectors, or any other suitable device for interpreting the readings obtained from the radiation detectors $412_1$ and $412_2$. For example, in embodiments where the radiation detectors $412_1$ and $412_2$ are ion chambers, the transmission cables $414_1$ and $414_2$ are cables for transmitting electrical signals, and the readout modules $416_1$ and $416_2$ are amplifiers which amplify the analog electric signal produced by the ion chamber. The ambient radiation monitor 400 also includes a coincidence detector 418 to which the readout modules $416_1$, $416_2$ are connected. The coincidence detector 418 is configured for operating in much the same way as the coincidence detector 117, described hereinabove.

The radiation detectors $412_1$, $412_2$ are positioned proximate the portion 200 of the body, for example on opposite sides thereof, and are proximate the scintillating coil 112. The radiation detectors $412_1$, $412_2$ are configured for monitoring the level of background radiation and/or the level of artificial ambient radiation in the vicinity of the portion 200. For example, the detectors $412_1$ and $412_2$ can monitor stray radiation that is incident to the portion 200 from a different part of the body. The timing parameter that is associated with a background radiation event detected with the radiation detectors $412_1$ and $412_2$ can be compared with the timing parameters that are associated with the radiation detected with the scintillating fiber coil 112. If the timing parameters match, then the signal detected with the scintillating coil 112 is rejected, as it originates from another part of the body than the portion 200.

In some embodiments, the ambient radiation monitor 400 is configured for monitoring the radiotracer activity in the portion 200. When a positron from the radiotracer interacts with an electron in the portion 200, two photons which travel in opposite directions are produced. The ambient radiation monitor 400, and more specifically the readout modules $416_1$ and $416_2$ and the coincidence detector 418 will be used to determine if the two photons originate from the same interaction event. The solid angle that the two radiation detectors $412_1$, $412_2$ span determines the subset of all photons from interaction events that can be detected. The solid angle, and the efficiency of the radiation detectors $412_1$, $412_2$, and the like, are used to determine the total radiotracer activity in the portion 200. In some embodiments, the radiation detectors $412_1$ and $412_2$ are composed of a scintillating material, which may be similar to the material used in the scintillating fiber coil 112. In some such embodiments, the radiation detectors $412_1$, $412_2$ and any associated light sensitive elements, for example the fiber optic cables $414_1$ and $414_2$ and the readout modules $416_1$ and $416_2$, are retained within a structure that substantially prevents stray photons from light sources, for example nearby lamps or the sun, from interfering with the photons $308_1$, $308_2$ travelling from the radiation detectors $412_1$ and $412_2$.

Figure 5:
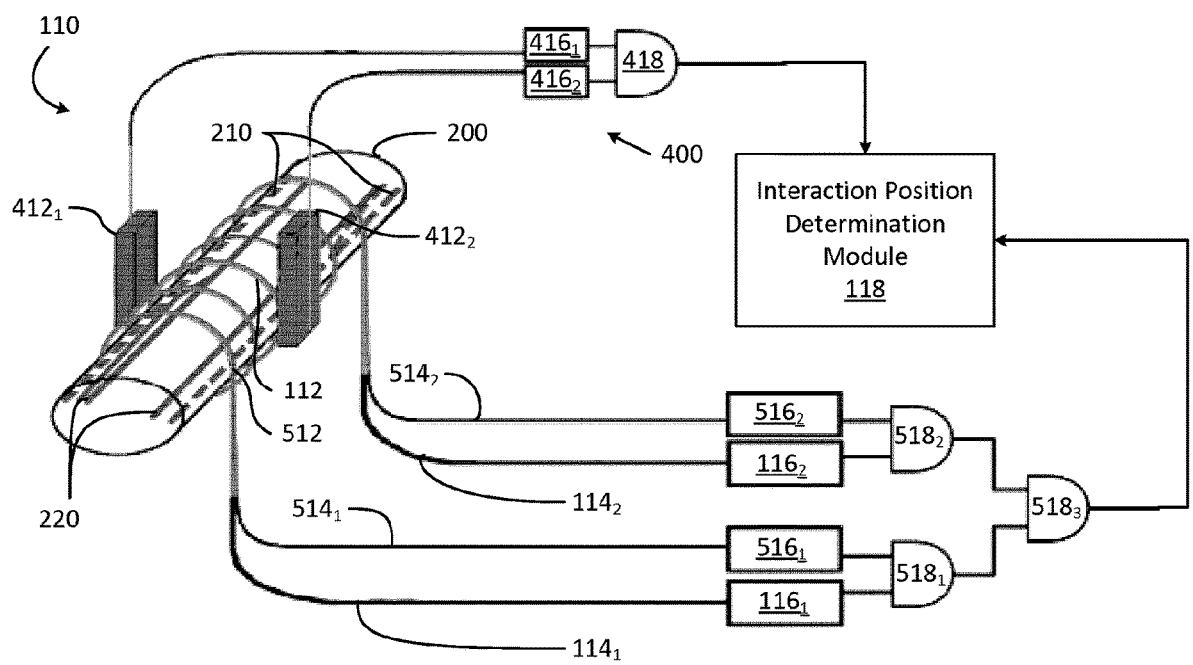
FIG. 5 is a block diagram illustrating a third embodiment of a radiotracer activity monitor.

With reference to FIG. 5, in some embodiments the radiotracer activity monitor 110 further includes one or more secondary scintillating fiber coils 512 to enhance or augment the precision of the determination of positions of interaction. The secondary scintillating fiber coil 512 is connected at first and second ends to secondary fiber optic cables $514_1$, $514_2$, which carry pluralities of photons generated within the secondary scintillating fiber coil to photon detectors $516_1$, $516_2$. In this embodiment, three cascaded coincidence detectors $518_1$-$518_3$ are included in the radiotracer activity monitor 110. It should be noted that the embodiment of the radiotracer activity monitor 110 shown in FIG. 5 may be provided with or without the ambient radiation monitor 400. The embodiment of FIG. 5 is used, for example, in situations of particularly high radiotracer activity in the portion 200.

In some embodiments, the secondary scintillating fiber coil 512 is substantially identical to the scintillating fiber coil 112, and is juxtaposed or adjacent thereto. For example, loops of the secondary scintillating fiber coil 512 can be concentric with the loops of the scintillating fiber coil 112. In other embodiments, the secondary scintillating fiber coil 512 differs from the scintillating fiber coil in one or more ways, for example length, size, curved pattern spacing, curved pattern count, material, and the like. Additionally, in some other embodiments, the secondary scintillating fiber coil 512 is separated from the scintillating fiber coil 112 via an isolator, which can be a layer of opaque material, to prevent or minimize the risk of photons bleeding from one scintillating fiber coil to the other.

In the embodiment shown in FIG. 5, the electrical signals output by the photon detectors $116_1$ and $516_1$ are fed to the first coincidence detector $518_1$, and the electrical signals output by the photon detectors $116_2$ and $516_2$ are fed to the second coincidence detector $518_2$. The coincidence detectors $518_1$ and $518_2$ output electrical signals which are sent to the third coincidence detector $518_3$, and the output of the third coincidence detector $518_3$ is sent to the interaction position determination module 118.

The cascaded coincidence detectors $518_1$-$518_3$ are used to ensure that the pluralities of photons received at the photon detectors $116_1$, $116_2$, $516_1$ and $516_2$ originate from a common set of interaction events. The cascade coincidence detectors $518_1$-$518_3$ therefore reduce the risk of associating overlapping photon pluralities that originate from different interaction events with one and another.

It should also be noted that, although the embodiment of FIG. 5 shows two separate scintillating fiber coils, 112 and 512, other embodiments of the radiotracer activity monitor 110 can include three, four, five, or more scintillating fiber coils, each with respective fiber optic cables and photon detectors. In addition, the cascaded coincidence detectors can be provided with additional levels to ensure that proper associations are made between received pluralities of photons.

In some embodiments, the length and/or loop count of the scintillating fiber coils 112, 512 is adjustable to compensate for the number of interaction events detected. For example, when too many interaction events are detected by the photon detectors $116_1$, $116_2$ and/or $516_1$, $516_2$, the scintillating fiber coils 112, 512 can be shortened and/or have loops removed therefrom. In the converse case, where too few interaction events are detected, the scintillating fiber coils 112, 512 can be lengthened and/or have loops added thereto. For example, the scintillating fiber coil 112 and/or 512 is composed of a plurality of sections, each having one or more loops, and sections can be removed or added to adjust for the required level of activity in the scintillating fiber coil 112 and/or 512.

In addition, in some embodiments a radiation shield or other protective device is placed over a section of the portion 200 to improve a positional resolution of the radiotracer activity monitor 110. The radiation shield is configured for blocking any emissions by the radiotracer, such as positrons, from propagating. For example, if the positions of interaction cannot be determined with sufficient precision, the radiation shield can be placed on a top surface of the portion 200 between the portion 200 and the scintillating fiber coil 112, thereby blocking any emitted particles from the top of the portion 200 from reaching the scintillating fiber coil. As a result, the scintillating fiber coil 112 receives positrons only from lateral surfaces of the portion 200, which can lead to increased positional resolution.

Figure 6:
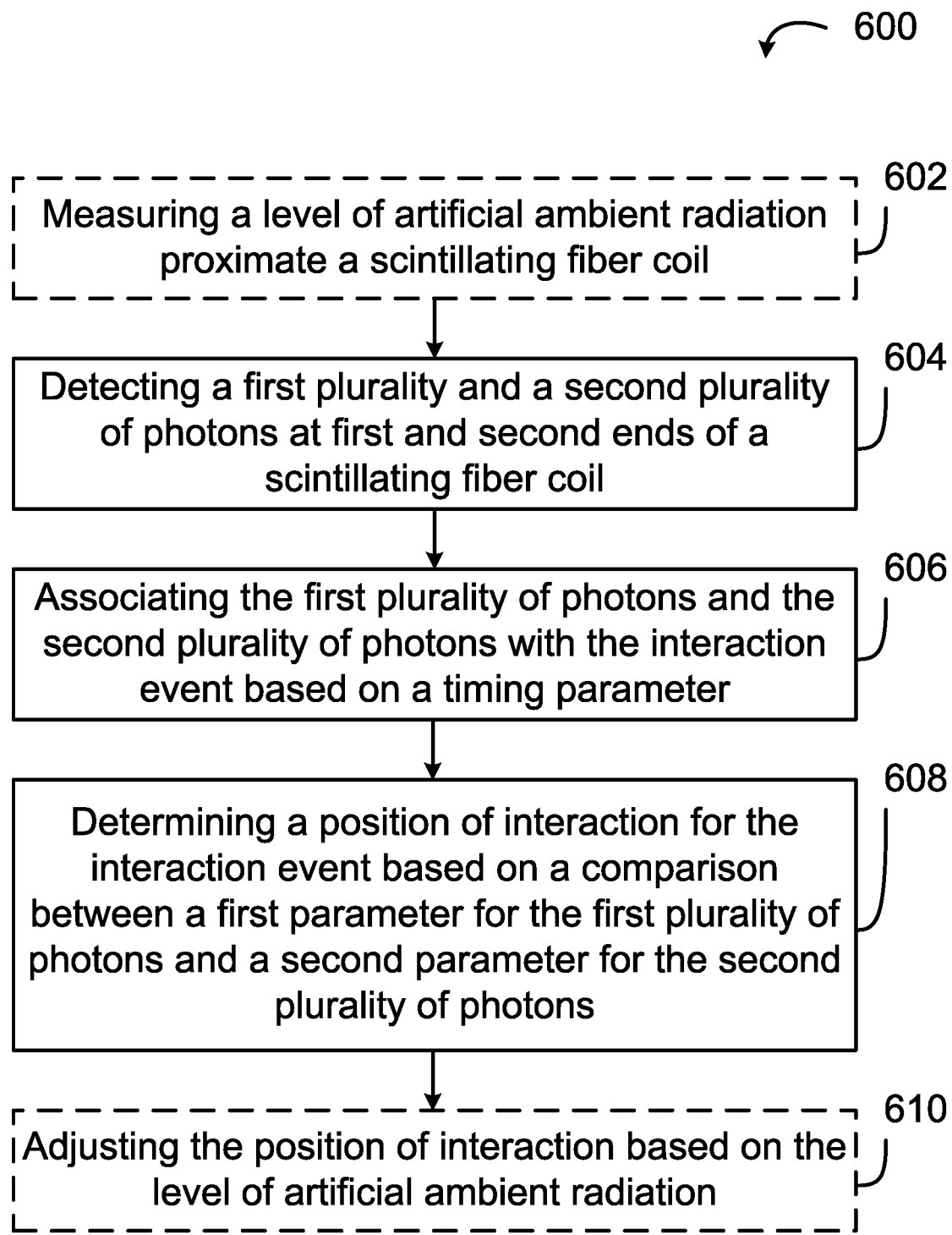
FIG. 6 is a flowchart of an example method for determining a position of interaction along a scintillating fiber coil.

With reference to FIG. 6, there is shown a method 600 for determining a position of interaction along a scintillating fiber coil, for example the scintillating fiber coil 112. The method 600 may be implemented by the radiotracer activity monitor 110. At step 602, optionally a level of artificial ambient radiation proximate a scintillating fiber coil, for example the scintillating fiber coil 112, is measured. The artificial ambient radiation can include radiation produced by the radiotracer in other parts of the body (i.e. outside the portion 200) and/or radiation produced by the radiotracer outside the artery 210 and/or the vein 220. The level of artificial ambient radiation proximate a scintillating fiber coil can be determined by the ambient radiation monitor 400, as described hereinabove.

At step 604, the radiotracer activity monitor 110 detects a first plurality and a second plurality of photons, for example the pluralities of photons $308_1$, $308_2$, at first and second ends 122, 124 of the scintillating fiber coil 112. The radiotracer activity monitor 110 detects the pluralities of photons $308_1$, $308_2$ using, for example, the photon detectors $116_1$, $116_2$.

At step 606, the radiotracer activity monitor 110 associates the first plurality of photons $308_1$ and the second plurality of photons $308_2$ with an interaction event based on a timing parameter. The interaction event, as described hereinabove, occurs when a radioactive particle, for example the positron 304 emitted by the radiotracer particle 302, collides or otherwise interacts with the scintillating fiber 112. For example, the association of the first plurality of photons $308_1$ and the second plurality of photons $308_2$ with the interaction event is performed by the interaction position determination module 118.

At step 608, a position of interaction for the interaction event is determined based on a comparison between first and second levels of attenuation to which the pluralities of photons $308_1$, $308_2$ were subjected. The position of interaction is a particular location along the scintillating fiber coil 112 where the positron interacted with one or more molecules 306 of the scintillating fiber coil 112. For example, the interaction position determination module 118 uses an algorithm or equation to determine the position of interaction based on the first and second levels of attenuation. In some embodiments, the levels of attenuation are determined based on first and second amplitudes of electrical signals produced by the photon detectors $116_1$, $116_2$ which are connected to the scintillating fiber coil 112.

Optionally, at step 610, the position of interaction is adjusted based on the level of artificial ambient radiation determined at step 602. In some embodiments, the adjustment includes adjusting the position value for the position of interaction, i.e. where along the scintillating fiber coil 112 the interaction occurred. In other embodiments, the adjustment includes discarding the position of interaction if the level of artificial ambient radiation indicates that the photons produced were a result of an interaction from a radiotracer particle outside the portion 200, the artery 210, and/or the vein 220. It should be noted that step 610 can be performed based on the results of 602 and/or based on the results of 604, 606 and 608, For example, during a time period before the radiotracer is administered, the scintillating fiber coil 112 measures the background signal that is spontaneously generated in the system. This type of background is sometimes referred to as dark background. In another example, during initial seconds after the radiotracer has been administered, the scintillating fiber coil 112 can measure "well-defined" signals in the artery 210 and vein 220 before the radiotracers have migrated into smaller vessels adjacent to the artery 210 and vein 220. In a further example, during a later portion of a monitoring period, the radiotracer activity monitor 110 uses the well-defined signals discussed in the preceding example (i.e., the signals that define the artery 210 and vein 220) to reject radiation events that originate from radiotracers that have migrated into the smaller vessels. These events may be considered as the artificial ambient radiation and be rejected.

Figure 7:
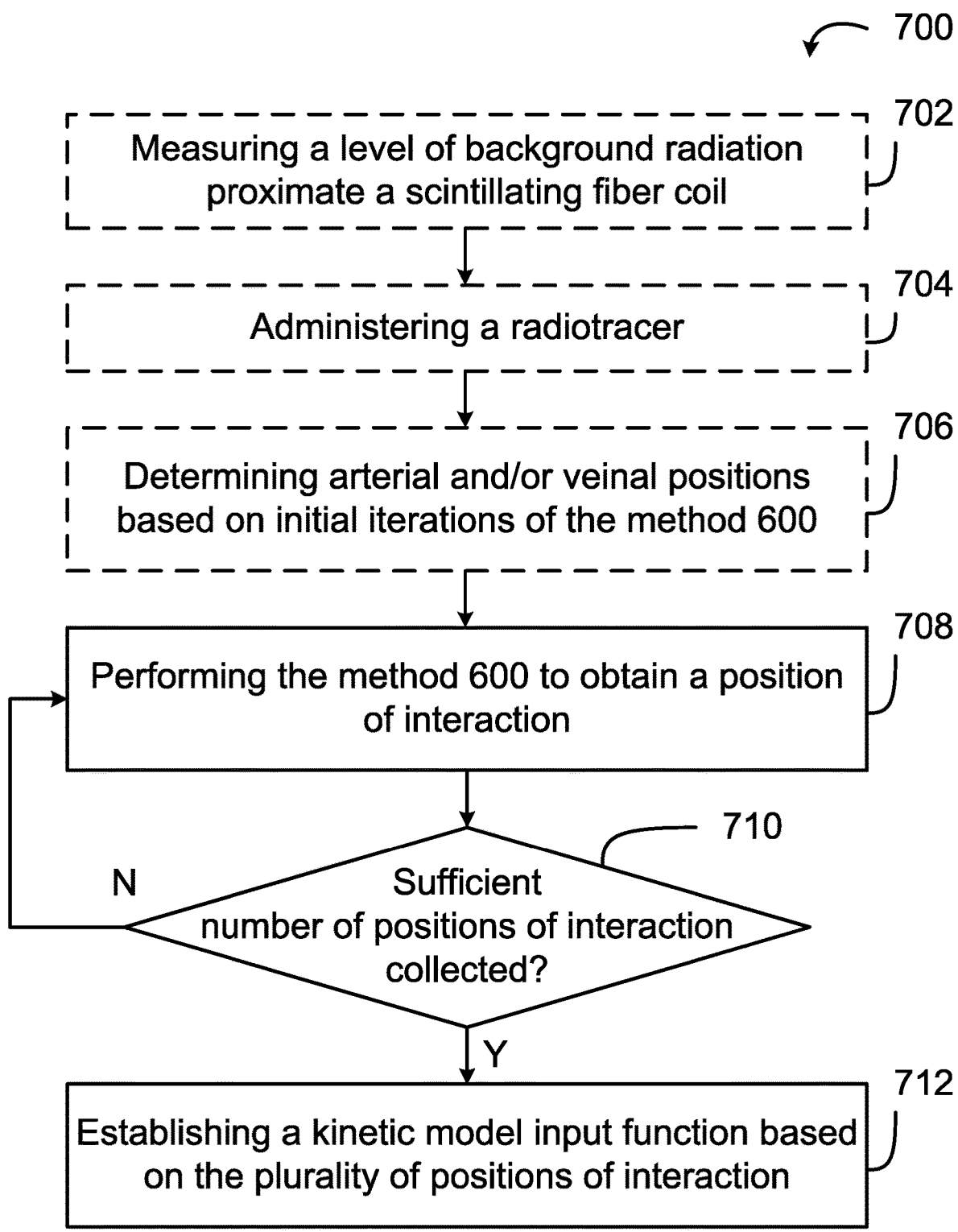
FIG. 7 is a flowchart of an example method for establishing a kinetic model IF in PET/SPECT/PET-MRI.

With reference to FIG. 7, there is shown a method 700 for establishing a kinetic model IF in PET/SPECT/PET-MRI. In some embodiments, the method 700 is implemented at least in part by the radiotracer activity monitor 110. Optionally, at step 702, a level of background radiation proximate the portion 200, and the scintillating fiber coil 112, is measured. For example, the background radiation level is measured by the ambient radiation monitor 400, or by the scintillating fiber coil 112, or by any other suitable background radiation detection system. The level of background radiation is provided, for example, to the interaction position determination module 118, or to any other suitable processing element of the radiotracer activity monitor 110.

Optionally, at step 704, a radiotracer is administered to a body, for example the body to which the portion 200 belongs. The radiotracer can be any suitable radiotracer having any suitable radioactive element, for example a positron-emitting radioisotope, which includes isotopes of any one or more of carbon, nitrogen, oxygen, fluorine, gallium, zirconium, rubidium, and the like, or a photon-emitting radioisotope, which includes technetium, indium, iodine, and the like. The radiotracer can be administered to the body in any suitable fashion, for example orally, intravenously, or in any other suitable fashion. In some embodiments, the radiotracer is administered directly to the artery 210.

Optionally, at step 706, one or more initial iterations of the method 600 are performed to determine positions for the artery 210 and/or the vein 220. Shortly after the radiotracer is administered, the radiotracer is largely confined to the artery 210 and/or the vein 220, for example until the heart or other circulatory system in the body has begun to circulate the radiotracer throughout the body. The method 600 can be performed one or more times and, with the radiotracer confined to the artery 210 and/or the vein 220, the positions of the artery 210 and/or the vein 220 can be determined based on the positions of interactions detected by the method 600. This can include optional steps 602 and 610, which use the ambient radiation monitor 400 to measure artificial ambient radiation produced by the radiotracer or other radioactivity in other parts of the body and/or in the portion 200 that does not originate from the artery 210 and/or the vein 220. In some embodiments, the ambient radiation monitor 400 measures a total amount of radioactivity produced within the portion 200, and the radioactivity measured by the scintillating fiber coil 112 of the radiotracer activity monitor 110 is adjusted based on the measurements obtained from the ambient radiation monitor 400.

At step 708, the method 600 is performed to collect a position of interaction. The position of interaction can be stored in a memory or other data storage element of the radiotracer activity monitor 110 in any suitable fashion. Decision step 710 determines whether a sufficient number of positions of interaction have been collected by the radiotracer activity monitor 110. If not, the method 700 returns to step 708, and the method 600 is repeated to collect an additional position of interaction. If a sufficient number of positions of interaction have been collected, the method 700 proceeds to step 712. The requirement for a sufficient number of positions of interaction may be a few dozen, a few hundred, a few thousand, or any other suitable number.

At step 712, a kinetic model IF is established based on the positions of interaction. The kinetic model IF can be established in any suitable way, using any suitable algorithm or calculation. In embodiments where optional step 702 is performed, the level of background radiation is also used as part of the algorithm for establishing the kinetic model IF. Additionally, in embodiments of the method 700 where steps 702 and/or 706 are performed, establishing the kinetic model IF may include adjusting the positions of interaction and/or other elements of the kinetic model IF based on the level of background radiation and/or the arterial and/or veinal positions.

In embodiments where the radiotracer activity monitor 110 is the embodiment illustrated in FIG. 5, therefore including the secondary scintillating coil 512 and the cascaded coincidence detectors $518_1$-$518_3$, the determination of the positions of interaction during the implementation of the method 600 at step 706 is performed based on the electrical signals received at both pairs of photon detectors $116_1$, $116_2$, and $516_1$, $516_2$. Thus, third and fourth pluralities of photons are received at the photon detectors $516_1$, $516_2$, in addition to the first and second pluralities of photons $308_1$, $308_2$ which are received by the photon detectors $116_1$, $116_2$, and the method 600 is performed for both the interaction events causing the first and second pluralities of photons $308_1$, $308_2$ and the interaction events causing the pluralities of photons received by the photon detectors $516_1$, $516_2$, and the kinetic model IF is based on both sets of positions of interaction.

Figure 8:
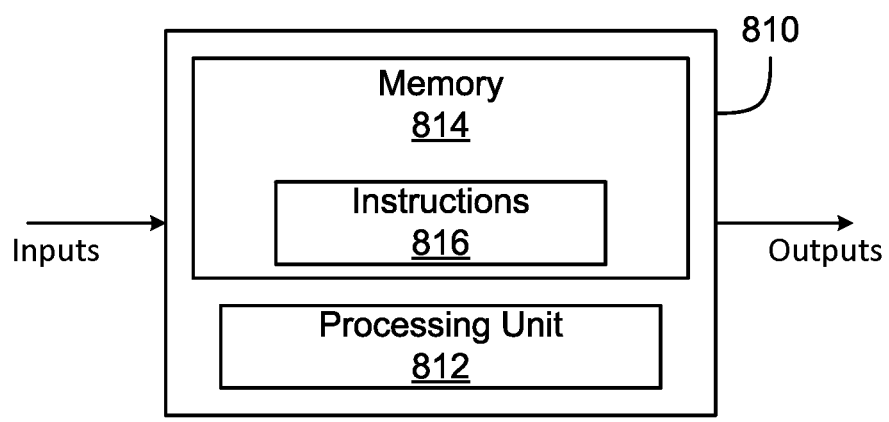
FIG. 8 is a schematic diagram of an embodiment of a computing system for implementing the method of FIGS. 6 and/or 7 in accordance with an embodiment.

With reference to FIG. 8, the methods 600 and/or 700 may be implemented by a computing device 810, comprising a processing unit 812 and a memory 814 which has stored therein computer-executable instructions 816. The processing unit 812 may comprise any suitable devices configured to implement the method 200 such that instructions 816, when executed by the computing device 810 or other programmable apparatus, may cause the functions/acts/steps of the method 200 described herein to be executed. The processing unit 812 may comprise, for example, any type of general-purpose microprocessor or microcontroller, a digital signal processing (DSP) processor, a central processing unit (CPU), an integrated circuit, a field programmable gate array (FPGA), a reconfigurable processor, other suitably programmed or programmable logic circuits, or any combination thereof.

The memory 814 may comprise any suitable known or other machine-readable storage medium. The memory 814 may comprise non-transitory computer readable storage medium, for example, but not limited to, an electronic, magnetic, optical, electromagnetic, infrared, or semiconductor system, apparatus, or device, or any suitable combination of the foregoing. The memory 814 may include a suitable combination of any type of computer memory that is located either internally or externally to device, for example random-access memory (RAM), read-only memory (ROM), compact disc read-only memory (CDROM), electro-optical memory, magneto-optical memory, erasable programmable read-only memory (EPROM), and electrically-erasable programmable read-only memory (EEPROM), Ferroelectric RAM (FRAM) or the like. Memory 814 may comprise any storage means (e.g., devices) suitable for retrievably storing machine-readable instructions 816 executable by processing unit 812.

In some embodiments, a single computing device, such as the computing device 810, can be used to implement any one or more of the scan analyzer 104, the radiotracer activity monitor 110, and the interaction position determination module 118. In other embodiments, separate computing devices, for example the computing device 810, are provided for each of the scan analyzer 104, the radiotracer activity monitor 110, and the interaction position determination module 118.

The methods and systems for determining a position of interaction along a scintillating fiber coil and for establishing a kinetic model IF in PET/SPECT/PET-MRI described herein may be implemented in a high level procedural or object oriented programming or scripting language, or a combination thereof, to communicate with or assist in the operation of a computer system, for example the computing device 810. Alternatively, the methods and systems for determining a position of interaction along a scintillating fiber coil and for establishing a kinetic model IF in PET/SPECT/PET-MRI may be implemented in assembly or machine language. The language may be a compiled or interpreted language. Program code for implementing the methods and systems for controlling operation of the deprime valve may be stored on a storage media or a device, for example a ROM, a magnetic disk, an optical disc, a flash drive, or any other suitable storage media or device. The program code may be readable by a general or special-purpose programmable computer for configuring and operating the computer when the storage media or device is read by the computer to perform the procedures described herein. Embodiments of the methods and systems for determining a position of interaction along a scintillating fiber coil and for establishing a kinetic model IF in PET/SPECT/PET-MRI may also be considered to be implemented by way of a non-transitory computer-readable storage medium having a computer program stored thereon. The computer program may comprise computer-readable instructions which cause a computer, or more specifically the processing unit 812 of the computing device 810, to operate in a specific and pre-defined manner to perform the functions described herein.

Computer-executable instructions may be in many forms, including program modules, executed by one or more computers or other devices. Generally, program modules include routines, programs, objects, components, data structures, etc., that perform particular tasks or implement particular abstract data types. Typically the functionality of the program modules may be combined or distributed as desired in various embodiments.

The above description is meant to be exemplary only, and one skilled in the relevant arts will recognize that changes may be made to the embodiments described without departing from the scope of the invention disclosed. For example, the blocks and/or operations in the flowcharts and drawings described herein are for purposes of example only. There may be many variations to these blocks and/or operations without departing from the teachings of the present disclosure. For instance, the blocks may be performed in a differing order, or blocks may be added, deleted, or modified. While illustrated in the block diagrams as groups of discrete components communicating with each other via distinct data signal connections, it will be understood by those skilled in the art that the present embodiments are provided by a combination of hardware and software components, with some components being implemented by a given function or operation of a hardware or software system, and many of the data paths illustrated being implemented by data communication within a computer application or operating system. The structure illustrated is thus provided for efficiency of teaching the present embodiment. The present disclosure may be embodied in other specific forms without departing from the subject matter of the claims. Also, one skilled in the relevant arts will appreciate that while the systems, methods and computer readable mediums disclosed and shown herein may comprise a specific number of elements/components, the systems, methods and computer readable mediums may be modified to include additional or fewer of such elements/components. The present disclosure is also intended to cover and embrace all suitable changes in technology. Modifications which fall within the scope of the present invention will be apparent to those skilled in the art, in light of a review of this disclosure, and such modifications are intended to fall within the appended claims.

The invention claimed is:

1. A method for determining a position of interaction along a scintillating fiber coil, comprising:
   positioning the scintillating fiber coil to substantially cover a portion of a body;
   detecting a first plurality and second plurality of photons at first and second ends of the scintillating fiber coil, respectively, the first and second pluralities of photons produced by an interaction event between a radiotracer and the scintillating fiber coil;
   associating the first plurality of photons and the second plurality of photons with the interaction event based on a timing parameter; and
   determining a position of interaction for the interaction event based on a comparison between a first parameter of the first plurality of photons and a second parameter of the second plurality of photons.

2. The method of claim 1, further comprising measuring a level of background radiation proximate the scintillating fiber coil, wherein determining a position of interaction comprises adjusting the first and second levels of attenuation based on the level of background radiation.

3. The method of claim 1, wherein detecting the first plurality and second plurality of photons produced by the scintillating fiber coil comprises receiving the first and second pluralities of photons via an optical fiber.

4. The method of claim 3, wherein an attenuation coefficient of the optical fiber is lower than an attenuation coefficient of the scintillating fiber coil.

5. The method of claim 1, wherein detecting the first plurality and second plurality of photons produced by the scintillating fiber coil comprises determining, via a coincidence detector, that the first plurality of photons and the second plurality of photons are produced by the interaction event based on a time of receipt of the first plurality of photons and of the second plurality of photons.

6. The method of claim 1, wherein the first and second parameters are first and second attenuation levels, respectively.

7. The method of claim 1, wherein the portion of the body is a wrist.

8. The method of claim 1, further comprising administering the radiotracer.

9. A method for establishing a kinetic model input function in one of positron emission tomography and single-photon emission computed tomography, comprising:
   determining a plurality of positions of interaction along a scintillating fiber coil, the scintillating fiber coil arranged for substantially covering a portion of a body, by:
     detecting a first plurality and second plurality of photons at first and second ends of the scintillating fiber coil, respectively, the first and second pluralities of photons produced by an interaction event between a radiotracer and the scintillating fiber coil;
     associating the first plurality of photons and the second plurality of photons with the interaction event based on a timing parameter; and
     determining a position of interaction for the interaction event based on a comparison between a first parameter of the first plurality of photons and a second parameter of the second plurality of photons; and
   establishing the kinetic model input function based on the plurality of positions of interaction.

10. A device for establishing a kinetic model input function in positron emission tomography and single-photon emission computed tomography, comprising:
    a scintillating fiber coil arranged for substantially covering a portion of a body, the scintillating fiber coil having a first end and a second end;
    at least one photon detector optically connected to the first and second ends of the scintillating fiber coil; and
    a processing device communicatively coupled to the at least one photon detector and configured for:
      for each of a plurality of interaction events between the scintillating fiber coil and a radiotracer in the body:
        detecting first and second pluralities of photons at first and second ends of the scintillating fiber coil, respectively, the first and second pluralities of photons produced by the interaction event;
        associating the first plurality of photons and the second plurality of photons with the interaction event based on a timing parameter; and
        determining a position of interaction for the interaction event based on a comparison between a first parameter of the first plurality of photons and a second parameter of the second plurality of photons; and
      establishing the kinetic model input function based on the positions of interaction.

11. The device of claim 10, further comprising an ambient radiation monitor communicatively coupled to the processing device, wherein the processing device is further configured for obtaining a measurement of a level of background radiation proximate the scintillating fiber coil from the ambient radiation monitor, and wherein determining a position of interaction comprises adjusting the first and second levels of attenuation based on the level of background radiation.

12. The device of claim 10, wherein the level of background radiation comprises radiation produced by the body.

13. The device of claim 10, further comprising an optical fiber, wherein the at least one photon detector is optically connected to the first and second ends of the scintillating fiber coil via the optical fiber.

14. The device of claim 13, wherein an attenuation coefficient of the optical fiber is lower than an attenuation coefficient of the scintillating fiber coil.

15. The device of claim 10, further comprising a coincidence detector, wherein the processing device is configured for operating the coincidence detector to detect the first plurality and second plurality of photons produced by the scintillating fiber coil to determine that first plurality of photons and the second plurality of photons are produced by the interaction event based on a time of receipt of the first plurality of photons and of the second plurality of photons.

16. The device of claim 10, wherein the first and second parameters are first and second attenuation levels, respectively.

17. The device of claim 10, wherein the portion of the body is a wrist.

18. The device of claim 10, further comprising a subsequent scintillating fiber coil optically connected to the at least one photon detector, wherein the processing device is further configured for performing the steps of detecting, associating, and determining for third and fourth pluralities of photons for a subsequent plurality of interaction events between the subsequent scintillating fiber coil and the radiotracer.

19. The device of claim 18, wherein the subsequent scintillating fiber coil is arranged for substantially covering a subsequent portion of the body at least in part different from the portion of the body.

* * * * *